United States Patent
Ono

(10) Patent No.: US 9,651,767 B2
(45) Date of Patent: May 16, 2017

(54) IMAGE PROCESSING APPARATUS FOR ENDOSCOPE, ENDOSCOPE SYSTEM AND IMAGE PROCESSING METHOD FOR ENDOSCOPE

(71) Applicant: OLYMPUS CORPORATION, Shibuya-ku, Tokyo (JP)

(72) Inventor: Mitsunobu Ono, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 700 days.

(21) Appl. No.: 13/974,522

(22) Filed: Aug. 23, 2013

(65) Prior Publication Data
US 2014/0375781 A1    Dec. 25, 2014

(30) Foreign Application Priority Data
Jun. 21, 2013 (JP) ................... 2013-130298

(51) Int. Cl.
| A61B 1/04 | (2006.01) |
| H04N 5/30 | (2006.01) |
| H04N 5/335 | (2011.01) |
| H04N 5/225 | (2006.01) |
| G02B 23/24 | (2006.01) |
| A61B 1/00 | (2006.01) |

(Continued)

(52) U.S. Cl.
CPC ...... *G02B 23/2484* (2013.01); *A61B 1/00009* (2013.01); *A61B 1/00059* (2013.01); *A61B 1/045* (2013.01); *A61B 1/05* (2013.01)

(58) Field of Classification Search
CPC ......... H04N 7/18; G02B 23/2484; A61B 1/04
See application file for complete search history.

(56) References Cited

U.S. PATENT DOCUMENTS

| 5,278,656 A * | 1/1994 | Hynecek ............... H04N 5/335 348/207.99 |
| 6,774,930 B2 | 8/2004 | Tashiro et al. |
| 7,773,110 B2 | 8/2010 | Abe |

(Continued)

FOREIGN PATENT DOCUMENTS

| JP | 10210360 A | 8/1998 |
| JP | 2001070241 A | 3/2001 |

(Continued)

OTHER PUBLICATIONS

Japanese Office Action (and English translation thereof) dated Mar. 28, 2017 issued in counterpart Japanese Application No. 2013-130298.

*Primary Examiner* — Sath V Perungavoor
*Assistant Examiner* — Patricia I Young
(74) *Attorney, Agent, or Firm* — Holtz, Holtz & Volek PC

(57) ABSTRACT

An image processing apparatus for an endoscope, the image processing apparatus to which, any of a plurality of insertion units respectively having imaging devices with numbers of pixels different from one another being installed therein, is detachably connected and which processes an image signal captured by that imaging device and outputs the processed image signal as image data, the image processing apparatus including: an image signal processing unit that converts a pixel density of the image signal to a high density and generates a standard image signal of a predetermined amount of data.

4 Claims, 6 Drawing Sheets

(51) Int. Cl.
*A61B 1/045* (2006.01)
*A61B 1/05* (2006.01)

(56) References Cited

U.S. PATENT DOCUMENTS

| | | |
|---|---|---|
| 2003/0025789 A1 | 2/2003 | Tashiro et al. |
| 2005/0024508 A1 | 2/2005 | Okisu et al. |
| 2005/0231591 A1 | 10/2005 | Abe |
| 2013/0162819 A1* | 6/2013 | Wang ............... H04N 17/004 348/143 |

FOREIGN PATENT DOCUMENTS

| | | |
|---|---|---|
| JP | 2005-118159 A | 5/2005 |
| JP | 2005296534 A | 10/2005 |

* cited by examiner

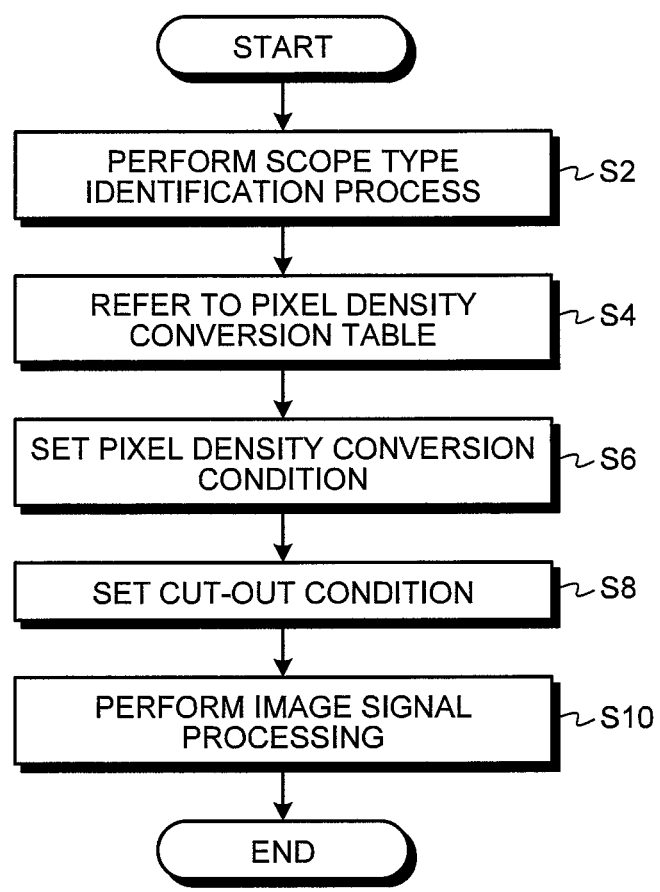

1H=ABOUT 55 μ sec, 60 fields/sec

1H=ABOUT 30 μ sec, 60 fields/sec

| SCOPE | PIXEL DENSITY CONVERSION MAGNIFICATION | DUMMY SIGNAL SUPPLEMENTING AREA | DUMMY SIGNAL EXCLUDING AREA | CUT-OUT AREA |
|---|---|---|---|---|
| 2A | 3.44 | Sb | Sb | Sa |
| 2B | 1.0 | NO | NO | ENTIRE Ug |

IMAGE PROCESSING APPARATUS FOR ENDOSCOPE, ENDOSCOPE SYSTEM AND IMAGE PROCESSING METHOD FOR ENDOSCOPE

CROSS REFERENCES TO RELATED APPLICATIONS

This application is based upon and claims the benefit of priority from Japanese Patent Application No. 2013-130298, filed on Jun. 21, 2013, the entire contents of which are incorporated herein by reference.

BACKGROUND OF THE INVENTION

1. Field of the Invention

The present invention relates to: an image processing apparatus for an endoscope, the image processing apparatus to which, any of a plurality of insertion units respectively having imaging devices with numbers of pixels different from one another mounted therein, is detachably connected and which processes an image signal captured by that imaging device to output the processed image signal as image data; an endoscope system; and an image processing method for an endoscope.

2. Description of the Related Art

Conventionally, endoscope apparatuses have been widely used for various tests in the medical field and the industrial field. For example, in the industrial field, endoscope apparatuses are used to perform tests in various environments such as internal tests of jet engines of aircrafts, internal tests of industrial plants, and tests of outdoor buildings. An endoscope apparatus is configured of: a scope having an elongated shape and an imaging device such as a CCD provided at a distal end thereof; and a main apparatus that processes an image captured by the imaging device. When a user of the endoscope apparatus inserts the scope inside an object to be tested, the image captured by the imaging device at the distal end of the scope is displayed on a monitor of the main apparatus, and the image is stored in a recording medium.

In recent years, as a result of higher integration in imaging devices due to development of the semiconductor technology, imaging devices having a larger number of pixels (for example, 1.3 mega pixels) than conventionally used are now installable at the distal ends of the scopes. Therefore, an endoscope apparatus, to which plural types of scopes are detachably connected, and for which a scope among these various scopes is selectable according to a test object or a test environment, is now being practically applied.

In such an endoscope apparatus, since imaging devices are driven at frequencies appropriate for their respective numbers of pixels, a plurality of internal operating clocks are settable according to types of imaging devices of scopes connected to its main apparatus. In addition, in the main apparatus, plural circuits for image signal processing are provided according to the imaging devices. In that case, if a circuit is provided for each imaging device, the circuit scale becomes complicated and the structure of the apparatus becomes large.

Therefore, in order to avoid complication of the circuits in the main apparatus, an endoscope apparatus, which performs each signal processing after down-converting the number of pixels of an image output from the imaging device to the number of pixels that is processable by an internal processor of the main apparatus, has been proposed (for example, see Japanese Laid-open Patent Publication No. 2005-118159).

SUMMARY OF THE INVENTION

According to an aspect of the present invention, an image processing apparatus for an endoscope is an image processing apparatus to which, any of a plurality of insertion units respectively having imaging devices with numbers of pixels different from one another being installed therein, is detachably connected and which processes an image signal captured by that imaging device and outputs the processed image signal as image data. The image processing apparatus includes: an image signal processing unit that converts a pixel density of the image signal to a high density and generates a standard image signal of a predetermined amount of data.

According to another aspect of the present invention, an endoscope system includes: the image processing apparatus; and a plurality of insertion units, each detachably connectable to the image processing apparatus, the plurality of insertion units respectively having imaging devices with numbers of pixels different from one another installed therein.

According to still another aspect of the present invention, an image processing method for an endoscope includes: processing an image signal captured by an imaging device of an insertion unit connected to a main apparatus of an endoscope apparatus among a plurality of insertion units respectively having imaging devices with numbers of pixels different from one another installed therein; and outputting the processed image signal as image data; wherein the processing includes image signal processing of converting a pixel density of the image signal to a high density and generating a standard image signal of a predetermined amount of data.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 2 is a flowchart illustrating a processing procedure of an imaging process of the endoscope system illustrated in FIG. 1;

DETAILED DESCRIPTION OF THE PREFERRED EMBODIMENTS

Figure 1:
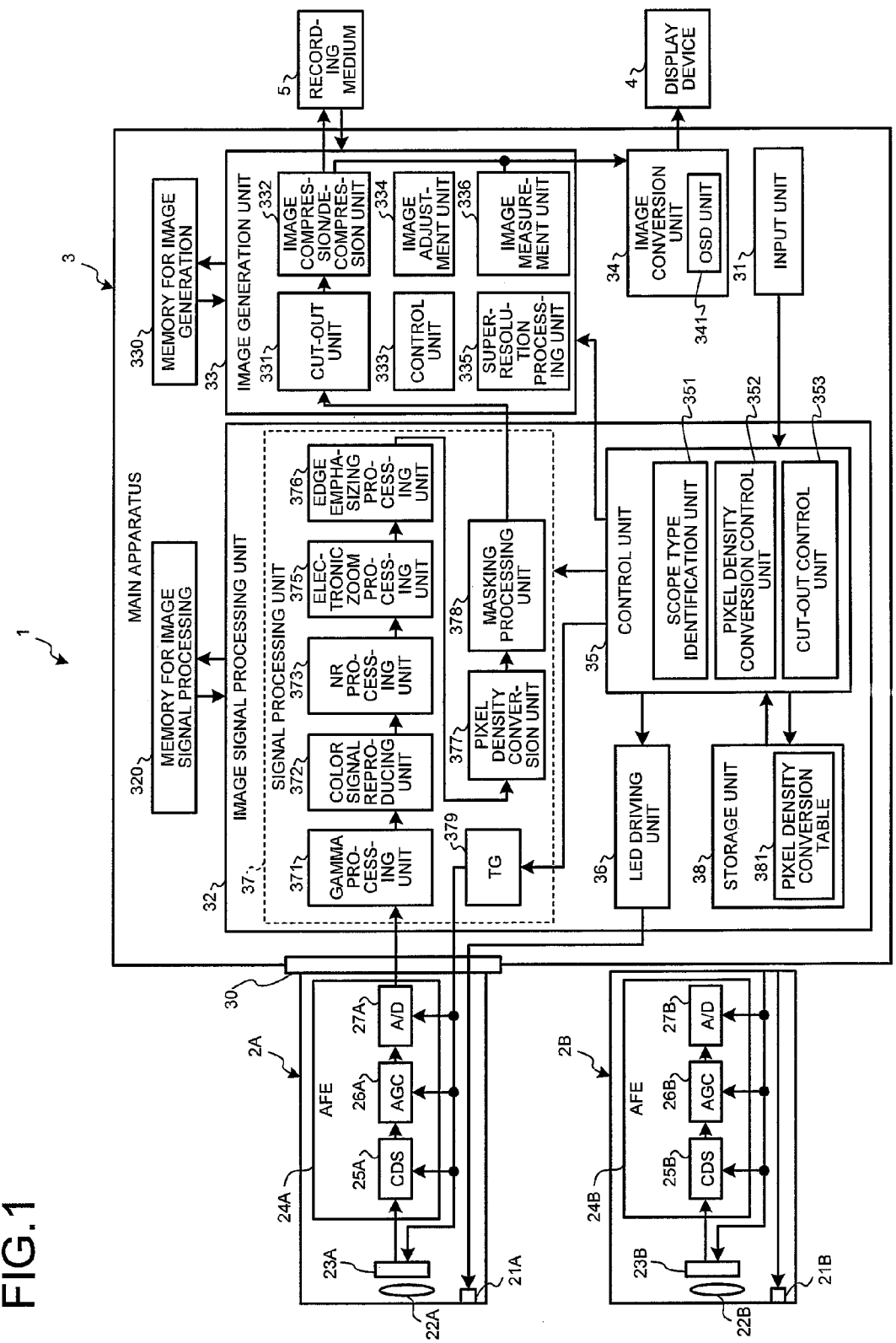
FIG. 1 is a block diagram illustrating a configuration of an endoscope system according to an embodiment of the present invention.

Hereinafter, an embodiment of an industrial endoscope system where imaging devices which capture a test object are installed at the distal end thereof will be described. The present invention is not limited to the embodiment. In the drawings, the same components are denoted by the same reference numerals.

FIG. 1 is a block diagram illustrating a configuration of an endoscope system according to the embodiment. As illustrated in FIG. 1, an endoscope system 1 according to the embodiment is configured to include scopes 2A and 2B which are inserted into a test object to capture images of the test object, a main apparatus 3 which one of the scopes 2A and 2B is detachably connected to and which processes an image signal captured by the connected scope to output image data, a display device 4 which display the image captured by the scope connected to the main apparatus 3, and a recording medium 5 which records the image captured by the scope. FIG. 1 exemplifies the case where the scope 2A of the scopes 2A and 2B is connected to the main apparatus 3.

The scope 2A is formed in an elongated shape having flexibility and functions as an insertion unit in the Claims. An LED 21A which emits illumination light illuminating the test object, an objective lens 22A which is installed inside of an observation window (not illustrated), and an imaging device 23A which is located at the focal point of the objective lens 22A are disposed at the distal end of the scope 2A. The imaging device 23A is constructed with a CCD where pixels which receive light and perform photo-electric conversion to generate an electric signal are arranged in a two-dimensional matrix shape. Similarly to the scope 2A, the scope 2B is formed in an elongated shape having flexibility, and an LED 21B, an objective lens 22B which is installed inside the observation window (not illustrated), and an imaging device 23B which is located at the focal point of the objective lens 22B are disposed at the distal end of the scope 2B. The imaging devices 23A and 23B are different from each other in the number of pixels. For example, the imaging device 23A has 0.44 mega pixels, and the imaging device 23B has 1.3 mega pixels. In addition, the scopes 2A and 2B are different from each other in scope diameter. The scope diameter of the scope 2B is larger than that of the scope 2A. In addition, the imaging devices 23A and 23B may be constructed with a CMOS. In addition, in the description of the embodiment, the case where the maximum number of pixels of the endoscope system 1 is 1.3 mega pixels is exemplified.

An analog front end unit (hereinafter, referred to as an "AFE unit") 24A which perform noise reduction or A/D conversion on the image signal output by the imaging device 23A is installed in the vicinity of a detachable portion of the proximal end of the scope 2A which is to be attached to/detached from the main apparatus 3. The AFE unit 24A is configured to include a CDS circuit 25A which reduces noise components included in an analog image signal by using, for example, a correlated double sampling method, an AGC (Automatic Gain Control) circuit 26A which maintains a constant output level by adjusting an amplification ratio (gain) of an electric signal, and an A/D conversion circuit 27A which performs A/D conversion on the image signal as image information output through the AGC circuit 26A. Similarly, an AFE unit 24B which is configured to include a CDS circuit 25B, an AGC circuit 26B, and an A/D conversion circuit 27B is installed in the vicinity of a detachable portion of the proximal end of the scope 2B. In addition, the AFE units may also be installed at the main apparatus 3 side instead of the scope side. In addition, the AFE units 24A and 24B may be embedded with respective timing generators for driving the corresponding imaging devices 23A and 23B.

Identification mechanisms indicating types of the scopes are installed in the scopes 2A and 2B. As the identification mechanisms, there is a mechanism of changing a shape of the proximal end of the scope according to the type of the scope or a resistance portion of which resistance value is determined according to the type of the scope.

The main apparatus 3 processes the image signal captured by the imaging device installed in the connected scope among the scopes 2A and 2B to output image data. The main apparatus 3 is configured to include a connector 30 which detachably connects the proximal end of the scope 2A or the proximal end of the scope 2B to the main apparatus 3, an input unit 31 which receives an input of a command signal instructing operation of the endoscope system 1, an image signal processing unit 32 which processes image signal captured by the imaging device 23A or the imaging device 23B to generate a standard image signal having a predetermined amount of data, an image generation unit 33 which generates image data for recording based on the standard image signal generated by the image signal processing unit 32, and an image conversion unit 34 which converts the image data generated by the image generation unit 33 into image data for display. A recording medium such as an SD card or a recording medium 5 such as USB is detachably installed in the main apparatus 3, so that the image data generated by the image generation unit 33 may be recorded in the recording medium 5.

The connector 30 communicates the electric signal with the connected scope 2A or scope 2B. A sensing mechanism for sensing types of the scope connected to the main apparatus 3 is installed in the connector 30. As the sensing mechanism, there is a mechanism of sensing a shape of the proximal end of the scope or a mechanism of sensing a resistance value of a resistor included in the scope.

The input unit 31 includes input devices such as a keyboard, various buttons, various switches or pointing devices such as a mouse or a touch panel and inputs a command signal to the image signal processing unit 32 according to user's manipulation of the above-described devices.

The image signal processing unit 32 is configured to include a control unit 35 which controls various constituting circuits of the imaging devices 23A and 23B and the AFE units 24A and 24B of the connected scopes 2A and 2B, the image signal processing unit 32, and the image generation unit 33, an LED driving unit 36 which performs control of switching on and off the LED 21A or the LED 21B under the control of the control unit 35 in the case where the scope 2A or the scope 2B are in a connected state, a signal processing unit 37 which processes the image signal captured by the imaging device of the scope connected to the main apparatus 3, and a storage unit 38 which includes the below-described pixel density conversion table 381 to store various types of control information. The image signal processing unit 32 may be configured by using an FPGA (Field Programmable Gate Array). In addition, the image signal processing unit 32 may be configured by using a gate array. In addition, the image signal processing unit 32 may also be configured by using a general-purpose DSP (Digital Signal Processor) if the general-purpose DSP has necessary functions.

The control unit 35 controls the imaging devices 23A and 23B to perform imaging processes with the respective appropriate driving frequencies. The driving frequency of the imaging device 23A of which the number of pixels is smaller than that of the imaging device 23B is set to be lower than the driving frequency of the imaging device 23B. The control unit 35 is configured to include a scope type identification unit 351 which identifies based on a result of sensing of the connector 30 which one of the scopes 2A and 2B the scope connected to the connector 30 is, a pixel density conversion control unit 352 which controls a pixel density conversion process of a pixel density conversion unit 377 in the below-described signal processing unit 37, and a cut-out control unit 353 which controls a data cut-out process of the below-described image generation unit 33.

The signal processing unit 37 is configured to include a gamma processing unit 371 which performs gamma correction on a color signal, a color signal reproducing unit 372 which performs color correction for improving color reproducibility, an NR processing unit 373 which frequency-decomposes the image signal and performs a noise reduction process such as a coring process according to the frequency, and an electronic zoom processing unit 375 which trims a portion of the image corresponding to the image signal and magnifies the trimmed image, an edge emphasizing processing unit 376 which performs an edge emphasizing process, a pixel density conversion unit 377 which converts (up-converts) the pixel density of the image signal into a high density in time to generate a standard image signal so as to have a predetermined amount of data, a masking processing unit 378 which masks four corners of the image where noise is easily included, and a timing generator 379 (hereinafter, referred to as a "TG 39") which generates and outputs a driving signal appropriate for each of the imaging devices 23A and 23B under the control of the control unit 35. The signal processing unit 37 also performs basic image signal processing such as subtraction of an OB (Optical Black) value, a white balance correction, and synchronization. The image signal processing unit 32 is connected to, for example, a memory for image signal processing 320 constructed with DDR-DRAM to temporarily store the image signal in the memory for image signal processing 320 and performs various signal processes.

The pixel density conversion unit 377 up-converts the pixel density of the image signal and, subsequently, supplements a predefined dummy signal to have a predetermined amount of data, so that the standard image signal is generated. Since the number of pixels in the horizontal direction and the number of pixels in the vertical direction of the image signal are defined by respective predefined numbers, the standard image signal can be processed at a prescribed clock frequency. The prescribed clock frequency is equal to an operating frequency of the image generation unit 33 which is a process unit installed at the rear end of the image signal processing unit 32.

The image generation unit 33 is configured to include a cut-out unit 331 which removes the dummy signal supplemented by the pixel density conversion unit 377 from the standard image signal generated by the image signal processing unit 32 to cut out an effective data portion corresponding to the image of the test object and an image compression/decompression unit 332 which compresses/decompresses the effective data portion of the image cut out by the cut-out unit 331 according to a predefined format. For example, the image compression/decompression unit 332 compresses/decompresses the effective data portion of the image according to a moving picture file format based on a standard such as MPEG (Moving Picture Experts Group). The image generation unit 33 outputs the image data compressed/decompressed in a predefined format to the image conversion unit 34. In addition, the image generation unit 33 stores the image data compressed/decompressed in a predefined format in the recording medium 5 installed in the main apparatus 3. The image generation unit 33 is configured by using, for example, a high-performance multimedia processor having general purposes capable of performing an image compression/decompression process, image recording on the recording medium 5, and image reproduction. The image generation unit 33 is connected to, for example, a memory for image generation 330 constructed with DDR-DRAM to temporarily store the image data in the memory for image generation 330 and performs various types of processes. In addition, the image generation unit 33 processes the standard image signals output from the image signal processing unit 32 at a constant frequency irrespective of the number of pixels of each of the imaging devices of the scopes. In addition, the image compression/decompression unit 332 may also compress/decompress the effective data portion of the image in a still image data format based on a format such as JPEG (Joint Photographic Experts Group).

The image generation unit 33 is configured to further include a control unit 333 constructed with a CPU. Therefore, besides performing the control of the image generation unit 33, the image generation unit 33 can also perform the control of the input unit 31 of the main apparatus 3, the control of the below-described OSD unit 341, and the setting and control of each function of the image signal processing unit 32 or the signal processing unit 37. The image generation unit 33 is configured to further include an image adjustment unit 334, a super-resolution processing unit 335, and an image measurement unit 366. The image adjustment unit 334 performs various image quality adjusting processes such as a contour emphasizing process or a color emphasizing process on the image recorded in the recording medium 5 or the image displayed on the display device 4. Although the signal processing unit 37 has the same image processing function, since the image generation unit 33 side also has the same function, the image quality of only the image of the display device 4 side may be adjusted without change in image quality of the image recorded in the recording medium 5. For example, only the image quality of the display device 4 side may be adjusted according to various use environments such as a dazzling outdoor environment or a dim indoor environment. On the contrary, in this apparatus, only the image quality of the recording medium 5 side may be adjusted without change in image quality of the display device 4 side, so that the apparatus can appropriately cope with user's request. In addition, since the image generation unit 33 includes the super-resolution processing unit 335, the image generation unit 33 can perform higher-performance contour correction than the edge emphasizing processing unit 376 of the signal processing unit 37. For example, the super-resolution processing unit 335 can perform high-performance process such as a contour emphasizing process of suppressing noise and emphasizing a contour of only an arbitrary portion. In addition, the image generation unit 33 is configured to further include an image measurement unit 336 so as to calculate a distance between two positions on the image designated through the input unit 31, an area of a designated region, or the like. A result of the measurement of the image measurement unit 336 is displayed on the below-described OSD unit 341.

The image conversion unit 34 converts the number of pixels of the image data output from the image generation unit 33 in accordance with the number of pixels of the display device 4. The image conversion unit 34 is configured to include an OSD unit 341 which outputs characters, a menu, or the like to the display device 4 in a manner where the characters, a menu, or the like are superimposed on the image data. In order to prevent image problems such as character bleeding or blurring, the superimposing process of the OSD unit 341 is performed after the number-of-pixels conversion process is performed. In addition, in the case where the number of pixels of the image data output from the image generation unit 33 and the number of pixels of the display device 4 are equal to each other, the number-of-pixels conversion process of the image conversion unit 34 is unnecessary. In this case, the image data are transferred to the display device 4 as they are.

The storage unit 38 stores a pixel density conversion table 381 listing control conditions of the processes of the pixel density conversion unit 377 and the image generation unit 33. In the pixel density conversion table 381, for each type of the scopes 2A and 2B, the pixel density conversion magnification ratio and the dummy signal supplementing area in the pixel density conversion process performed by the pixel density conversion unit 377 are associated with the dummy signal excluding area and the cut-out area of the effective data portion of the image in the cut-out process performed by the image generation unit 33, respectively. The control unit 35 controls the pixel density conversion process of the pixel density conversion unit 377 and the cut-out process of the image generation unit 33 with reference to the pixel density conversion table 381 so that the process on the image signal or the image signal is performed according to the pixel density conversion magnification ratio, the dummy signal supplementing area, the dummy signal excluding area, and the cut-out area corresponding to the type of the connected scope.

The display device 4 displays the image data output by the main apparatus 3. The display device 4 is configured by using a liquid crystal display or an organic EL (Electro Luminescence) display. The display device 4 is connected to the main apparatus 3 through a video cable. The display device 4 is, for example, of an array standard of 640 pixels in the horizontal direction and 480 pixels in the vertical direction or of an array standard of 1024 pixels in the horizontal direction and 768 pixels in the vertical direction. In addition, the display device 4 may be configured so as to be built in the main apparatus 3.

Next, the imaging process of the main apparatus 3 illustrated in FIG. 1 will be described with reference to FIG. 2. FIG. 2 is a flowchart illustrating a processing procedure of the imaging process of the endoscope system 1 illustrated in FIG. 1. In FIG. 2, a process on an 1-frame image is described.

As illustrated in FIG. 2, first, in the control unit 35, a scope type identification unit 351 performs a scope type identification process of identifying the type of the connected scope based on a state of the sensing mechanism of the connector 30 (Step S2).

Subsequently, the control unit 35 refers to the pixel density conversion table 381 of the storage unit 38 (Step S4), and the pixel density conversion control unit 352 sets the pixel density conversion condition corresponding to the type of the scope identified by the scope type identification unit 351 among the conditions in the pixel density conversion table 381 as the condition of the pixel density conversion process in the image signal processing unit 32 (Step S6).

Next, the cut-out control unit 353 sets the cut-out condition corresponding to the type of the scope identified by the scope type identification unit 351 among the conditions of the pixel density conversion table 381 as the condition of the cut-out process in the image generation unit 33 (Step S8).

Subsequently, the control unit 35 controls the components to perform the image signal processing of capturing an image, processing the imaged signal, and outputting the image (Step S10). In the image signal processing, first, the imaging device of the connected scope performs the imaging process, and the image signal captured by the imaging device is output to the image signal processing unit 32 through the AFE unit. The signal processing unit 37 performs the image signal processing including a gamma process, a color signal reproducing process, an NR process, an electronic zoom process, an edge emphasizing process, a pixel density conversion process according to the condition set by the pixel density conversion control unit 352, and a masking process on the output image signal to generate a standard image signal and outputs the standard image signal to the image generation unit 33. The processes in the image signal processing are performed in parallel for each pixel. Next, the image generation unit 33 performs a cut-out process of cutting out an effective data portion of the image by excluding the dummy signal according to the condition set by the cut-out control unit 353 on the standard image signal generated by the image signal processing unit 32 and, subsequently, compresses/decompresses the cut-out effective data portion of the image in a predefined image format to generate image data. The image data output from the image generation unit 33 are converted so as to be matched with a display format by the image conversion unit 34, and subsequently, the image data are output from the display device 4 to be displayed. At this time, the control unit 35 may store the image data output from the image generation unit 33 in the recording medium 5. In addition, the control unit 35 always determines whether or not the scope is removed. In the case where it is determined that the scope is removed, the power supply is turned off immediately.

Figure 3A:
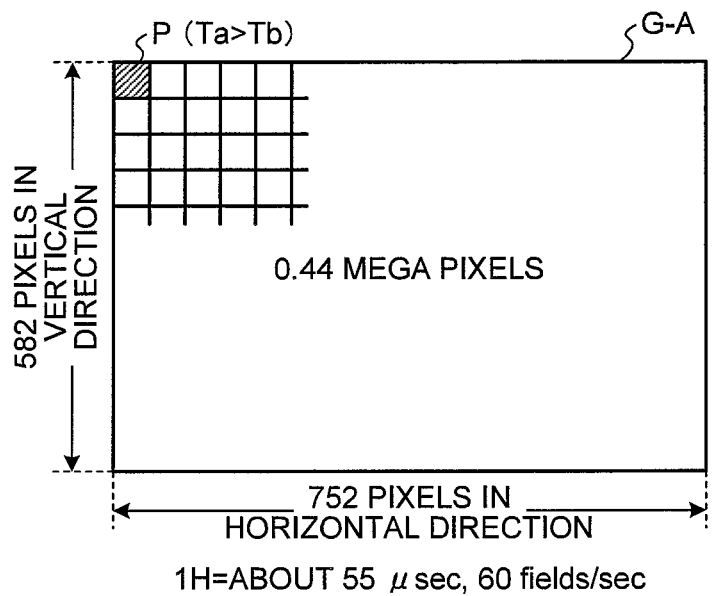
FIGS. 3A and 3B are schematic diagrams illustrating image signals generated by imaging devices illustrated in FIG. 1.
Figure 3B:
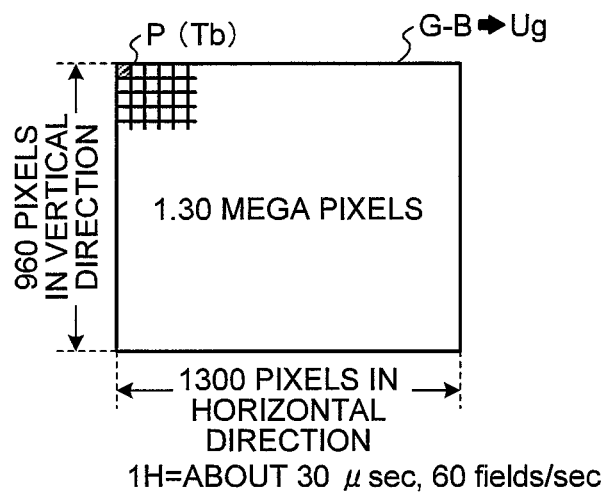

Next, the standard image signal will be described. First, the amount of data of the image signal generated by the imaging device 23A of the scope 2A and the amount of data of the image signal generated by the imaging device 23B of the scope 2B will be described. FIGS. 3A and 3B are schematic diagrams illustrating the image signals generated by the imaging devices 23A and 23B. The image signals are schematically illustrated so as to reflect a rate of read time per line. FIG. 3A illustrates the image signal generated by the imaging device 23A, and FIG. 3B illustrates the image signal generated by the imaging device 23B. In FIGS. 3A and 3B, for the description, the case where each of the imaging device 23A and the imaging device 23B outputs 60 fields of an image signal in units of 1 second is exemplified.

As illustrated in FIG. 3A, the image signal generated by the imaging device 23A G-A having 0.44 mega pixels is configured so that data of 582 pixels are arranged in the vertical direction and data of 752 pixels are arranged in the horizontal direction, and thus, the image signal is output at about 55 (μsec) per line (1H) including the blanking period. On the other hand, as illustrated in FIG. 3B, the image signal generated by the imaging device 23B G-B having 1.3 mega pixels is configured so that data of 960 pixels are arranged in the vertical direction and data of 1300 pixels are arranged in the horizontal direction, and thus, the image signal is output at about 30 (μsec) per line (1H) including the blanking period. In FIGS. 3A and 3B, since the rate of read time per line (1H) is reflected, a processing time Ta allocated to the data of 1 pixel P of the image signal G-A having a small number of pixels is larger than a processing time Tb allocated to the data of 1 pixel P of the image signal G-B having a large number of pixels. Therefore, at the time of inputting to the image signal processing unit 32, clock frequencies corresponding to the image signal G-A and the image signal G-B are different from each other. The clock frequency corresponding to the image signal G-A is lower than the clock frequency corresponding to the image signal G-B.

Therefore, in the embodiment, in order to process an image signal input to the image generation unit 33, which is captured by any imaging device, at a constant prescribed clock frequency, in the image signal processing unit 32 which is a processing circuit at the front end of the image generation unit 33, the standard image signal is generated by converting the pixel density of the image signal to a high density so as to have a predetermined amount of data. The standard image signal can be processed at the prescribed clock frequency, and a frequency having the same value as that of an operating frequency of the case where the image signal captured by the imaging device having the largest number of pixels is processed by the image generation unit 33 is set as the above-described prescribed clock frequency.

In the example of FIGS. 3A and 3B, a signal having a amount of data of the same pixels as those of the image signal G-B corresponding to the imaging device 23B having the maximum number of pixels, that is, 1.3 mega pixels in the endoscope system 1 is set as the normalized signal Ug (refer to FIG. 3B). Therefore, the normalized signal Ug is set so that the processing time allocated to each pixel P is Tb and so that data of 1300 pixels are arranged in the horizontal direction and data of 960 pixels are arranged in the vertical direction.

Figure 4:
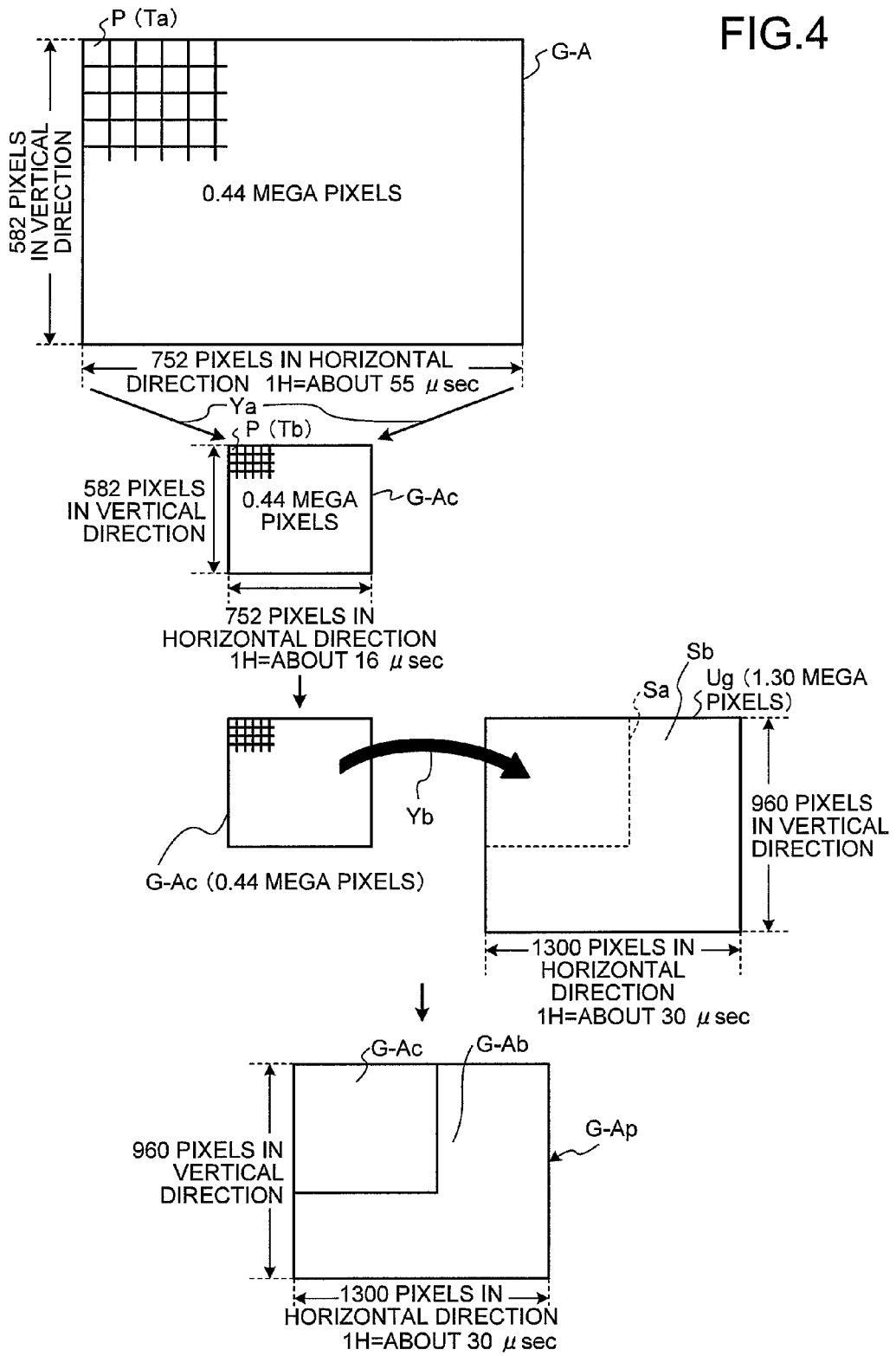
FIG. 4 is a diagram illustrating a pixel density conversion process of a pixel density conversion unit illustrated in FIG. 1.

The pixel density conversion unit 377 of the signal processing unit 37 performs a pixel density conversion process on the input image signal under the condition according to the types of the imaging devices 23A and 23B to generate a standard image signal which coincides with a amount of data of the normalized signal Ug and signal arrangement. FIG. 4 is a diagram illustrating the pixel density conversion process of the pixel density conversion unit illustrated in FIG. 1. Similarly to FIGS. 3A and 3B, the image signals are schematically illustrated so as to reflect a rate of read time per line (1H).

In the case where the input image signal is the image signal G-A having data of 0.44 mega pixels generated by the imaging device 23A, the pixel density conversion unit 377 up-converts the pixel density of the image signal G-A so that the processing time allocated to the data of 1 pixel P is Tb as indicated by the arrow Ya. As a result, the time Ta allocated to the data of each pixel P is reduced to the time Tb, and the image signal G-Ac is generated so that the time corresponding to the data per line (1H) is about 16 (μsec) including the blanking period. At this time, since the image signal G-Ac is generated not by down-converting the image signal G-A but by up-converting the image signal G-A, the data corresponding to 0.44 mega pixels of the image signal G-A can be retained without loss of the data.

Next, the pixel density conversion unit 377 disposes the data of the image signal G-Ac to the area Sa including the head position of the normalized signal Ug so that data of the pixels of the front end of the generated image signal G-Ac are located at the head position of the normalized signal Ug as indicated by the arrow Yb. Since the amount of data of the image signal G-Ac is smaller than that of the normalized signal Ug corresponding to the image signal corresponding to 1.3 mega pixels, the image signal G-Ac occupies only a partial area of the normalized signal Ug.

The pixel density conversion unit 377 supplements the dummy signal G-Ab to the area Sb where the data of the image signal G-Ac are not located to generate the standard image signal G-Ap of which the amount of data coincides with the amount of data of the normalized signal Ug. After the masking process is performed by the masking processing unit 378, the standard image signal G-Ap generated by the pixel density conversion unit 377 is output to the image generation unit 33. In addition, since the dummy signal is only supplemented in order to match the amount of data of the image signal transmitted from the image signal processing unit 32 to the image generation unit 33 with the amount of data of the normalized signal Ug, the dummy signal needs not to have specific information.

The operating frequency of the image generation unit 33 is set so that the image signal having an amount of data corresponding to 1.3 mega pixels which is the maximum number of pixels in the endoscope system 1 can be processed. In addition, the amount of data of the standard image signal G-Ap output from the signal processing unit 37 coincides with the amount of data of the normalized signal Ug corresponding to 1.3 mega pixels. Therefore, the image generation unit 33 can perform signal processing on the image signal G-Ap corresponding to the imaging device 23A having 0.44 mega pixels at the same frequency as the operating frequency of the case where a signal process is performed on the image signal having the amount of data corresponding to 1.3 mega pixels.

Figures 5, 6:
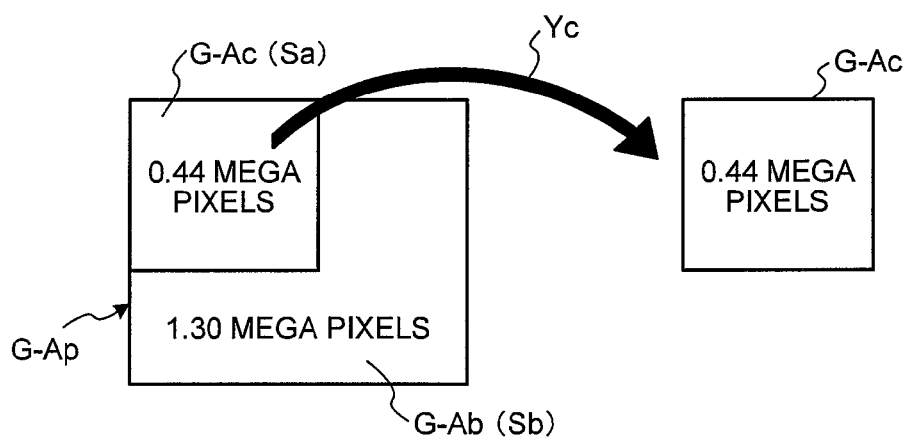
FIG. 5 is a diagram illustrating an image reproducing process of an image reproducing unit illustrated in FIG. 1.
FIG. 6 is a diagram illustrating an example of a pixel density conversion table illustrated in FIG. 1.

Next, a process of the image generation unit 33 illustrated in FIG. 1 will be described. FIG. 5 is a diagram illustrating an image reproducing process of the image reproducing unit illustrated in FIG. 1. Since the image signal G-Ap input to the image generation unit 33 includes a dummy signal G-Ab, first, the image generation unit 33 removes the data of the dummy signal G-Ab of the area Sb supplemented in the front end thereof from the data of the image signal G-Ap to cut out only the data of the area Sa as indicated by the arrow Yc. The data of the area Sa corresponds to the pixels data of the image signal G-Ac as effective image data. Next, the image generation unit 33 performs an image generation process on the data of the cut-out image signal G-Ac.

On the other hand, in the case where the image signal G-B captured by the imaging device 23B of the scope 2B is a processing object, the amount of data of the image signal G-B coincides with the amount of data of the normalized signal Ug. For this reason, with respect to the image signal G-B, the conversion magnification ratio of the pixel density conversion process of the pixel density conversion unit 377 becomes 1×, and the dummy signal supplementing is unnecessary. In addition, in the image generation unit 33, the entire normalized signal Ug is cut out as the effective data portion of the image as it is, and the image generation process is performed.

The process conditions of the processes of the pixel density conversion unit 377 and the image generation unit 33 performed as described above are stored in the pixel density conversion table 381 in a table format where the process conditions of the processes are in correspondence to the types of the scopes. FIG. 6 is a diagram illustrating an example of the pixel density conversion table 381 illustrated in FIG. 1.

Similarly the Table T1 illustrated in FIG. 6, the pixel density conversion table 381 is configured so that, with respect to each type of the scopes 2A and 2B, the pixel density conversion magnification ratio and the dummy signal supplementing area in the pixel density conversion process performed by the pixel density conversion unit 377 are associated with the dummy signal excluding area and the cut-out area of the effective data portion of the image in the cut-out process performed by the image generation unit 33. The control unit 35 allows the pixel density conversion unit 377 to perform the pixel density conversion process with reference to the table T1 according to the pixel density conversion magnification ratio, the dummy signal supplemented area, the dummy signal excluding area, and the cut-out area corresponding to the type of the connected scope and allows the image generation unit 33 to perform the cut-out process.

In the example of Table T1, in the case where the scope 2A is connected, the pixel density conversion magnification ratio of the pixel density conversion process becomes 3.44×, and the dummy signal supplementing area becomes the area Sb. In addition, in the cut-out process in the case where the scope 2A is connected, the dummy signal excluding area becomes the area Sb, and the cut-out area corresponding to the effective data portion of the image becomes the area Sa. In addition, in the case where the scope 2B is connected, the pixel density conversion magnification ratio of the pixel density conversion process becomes 1×, and since the dummy signal supplementing area is not set, the dummy signal supplementing process is unnecessary. In addition, in the cut-out process in the case where the scope 2B is connected, the dummy signal excluding area is not set, and the cut-out area corresponding to the effective data portion of the image becomes the entire normalized signal Ug.

In this manner, in the embodiment, since the image signal processing unit 32 up-converts the pixel densities of all the image signals so as to have a constant amount of data, in the image generation unit 33 at the rear end thereof, any image signal captured by any imaging device can be processed at a common constant clock frequency. Therefore, in the embodiment, it is sufficient that circuits and operation processes in a multimedia processor employed in the image generation unit 33 are configured so as to correspond to the standard image signal having a constant amount of data, so that the configuration of the apparatus can be simplified. In other words, in the embodiment, although the number of pixels of the imaging device of the scope connected to the main apparatus 3 is not constant, a multimedia processor can sufficiently process a standard image signal having a constant amount of data only by setting circuits and operation processes. Namely, according to the embodiment, since it is sufficient that the complicated high-functional image generation unit 33 can be designed and tested only by using a single type of a standard image signal, it is very advantageous in that the cost of development can be reduced and the time of development can be reduced.

In addition, the prescribed clock frequency is set according to the number of pixels of the imaging device of each scope connected to the main apparatus 3, and the normalized signal Ug has the same amount of data as that of the image signal G-B captured by the imaging device 23B which has the largest number of pixels among the imaging devices 23A and 23B of the scopes 2A and 2B connected to the main apparatus 3. Therefore, in the embodiment, even in the case where the scope 2B including the imaging device 23B having high resolution is selected, since the pixels data are not thinned out during the image process, the image where the resolution of the imaging device 23B of the scope 2B is retained can be output.

In addition, in the pixel density conversion process of the pixel density conversion unit 377, the case where the image signal G-Ac is disposed to the area Sa including the head position of the normalized signal Ug is described. If the disposed position of the image signal G-Ac is within the normalized signal Ug, although the image signal G-Ac is disposed at any position, the image generation process can be performed. Therefore, the image signal G-Ac may be disposed in an area which is far from the boundary of the normalized signal Ug.

Figure 7:
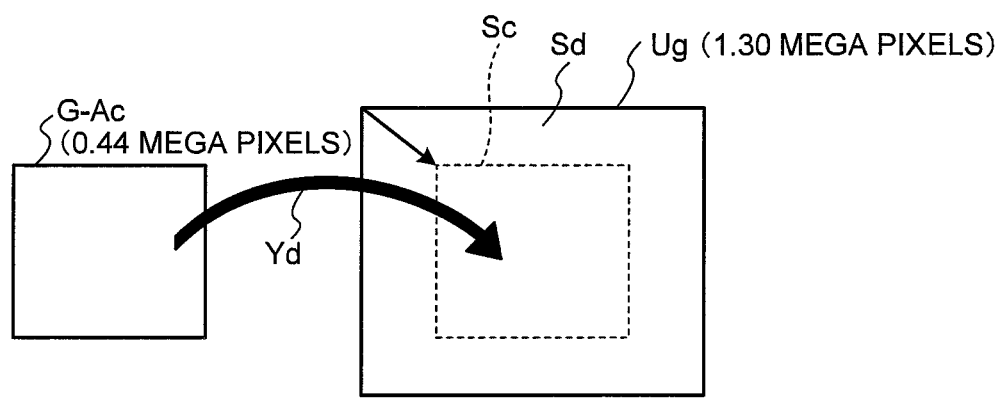
FIG. 7 is a diagram illustrating another example of the pixel density conversion process of the pixel density conversion unit illustrated in FIG. 1.

For example, as indicated by the arrow Yd in FIG. 7, the pixel density conversion unit 377 disposes the data of the pixel-density-converted image signal G-Ac in the area Sc, that is, an almost central area of the normalized signal Ug and supplements the dummy signal to the area Sd where the image signal G-Ac is not located. Namely, the dummy signal is supplemented so as to be located at the end portion of the normalized signal Ug. The image generation unit 33 cuts out only the effective image data located in the area Sc from the input standard image signal and performs the image generation process. As described above, in the case where the pixel density conversion unit 377 generates the standard image signal by supplementing the dummy signal so as to be located at the end portion of the normalized signal Ug, since the data of the effective image signal G-Ac as the image data can be located in an area which is far from the boundary of the normalized signal Ug, the influence of the noise generated in the vicinity of the boundary to the image can be removed, so that the output image can be stabilized.

In addition, as the amount of data of the normalized signal, the amount of data may be set so that the number of pixels of the normalized signal is larger than that of the image signal G-B. In this case, the pixel density conversion unit 377 up-converts all the image signal by a magnification ratio of 1× or more, disposes the effective data portion so as to be far from the boundary of the normalized signal, and supplements the dummy signal to the remaining area in the vicinity of the boundary. The dummy signal is supplemented so that any pixels constituting the effective data portion are not located at the boundary of the normalized signal. As a result, in the image generation unit 33, since the process of excluding the dummy signal from the vicinity of the boundary of the normalized signal is performed on all the image signals without use of the imaging device, the influence of noise generated in the vicinity of the boundary of the normalized signal can be securely removed. In addition, in addition to the determination of the amount of data of the normalized signal according to the number of pixels of the imaging device of the scope, the amount of data of the normalized signal may be determined depending on the processing capacity of the component circuits of the image generation unit 33.

In addition, in the embodiment, the prescribed clock frequency at which the standard image signal is processed is described as the driving frequency (clock) of the imaging device. In general, a recommended driving frequency is set correspondingly with the number of pixels of the imaging device. Besides the use of the recommended driving frequency, there is a case where a CCD is driven by slightly shifting an actual driving frequency from the recommended driving frequency, that is, a read process from the CCD is performed by slightly shifting the actual driving frequency from the recommended driving frequency. Herein, in the endoscope apparatus, since the physical size of the AFE unit is large, the AFE unit cannot be embedded in the front end portion of the endoscope insertion unit. Therefore, in general, an imaging sensor at the distal end of an insertion unit and the AFE unit are connected through the elongated insertion unit (electric cable). In this case, since the image signal is transmitted through the long electric cable, there is a case where the image signal passing the cable is attenuated or a case where distortion occurs in the signal due to the influence of noise. Particularly, in the boundary portions (up, down, left, and right portions) of the image, distortion occurs due to reflection of signal during the cable transmission, so that noise occurs. Therefore, there is a case where this portion is marked by a masking process (cutting). However, if the masking process is performed, an actual image output area is decreased, so that the size of the image is reduced, and thus, the value of the image is reduced. In order to avoid this problem, by slightly increasing the actual driving frequency from the predefined, recommended driving frequency according to the number of pixels of the imaging device, the process of reading apparently large number of pixels becomes effective. For example, extra two pixels in units of extra two lines in the vertical and horizontal directions in the vicinity of each effective pixel are read, and noise superimposed due to reflection in the cable or the like is allowed to occur in peripheral portion where extra two pixels in units of extra two lines in four directions are read. Subsequently, the peripheral portion is cut by performing the masking process in the signal processing unit 37, so that the effective pixels can be marked by 100%. In this case, since the number of read pixels is increased apparently, the read frequency of the CCD is slightly higher than the recommended driving frequency. More specifically, in the case of 0.44 mega pixels, a typical recommended driving frequency is 14.1875 MHz. However, an actual frequency used for reading the CCD is set to 15 MHz. In this manner, how many the number of read pixels is to be increased apparently is appropriately changed according to a length of the cable or a superimposed state of image noise in the circuit configuration.

The embodiment can be applied to the case where the frequency is set to slight higher than the recommended driving frequency in order to remove noise as described above. Namely, the embodiment is not limited to the case where the prescribed clock frequency is set to coincide completely with the recommended driving frequency (clock) of the imaging device having the maximum number of pixels. The frequency may be set to be slightly higher than recommended driving frequency of the imaging device having the maximum number of pixels so as to cope with the case where the imaging device is read out by setting the number of pixels for removing noise to be apparently more than the maximum number of pixels.

In addition, if the prescribed clock frequency of the standard image signal output from the image signal processing unit 32 is set so as to correspond to the maximum number of pixels read from the imaging device, since the frequency becomes smaller than the frequency corresponding to the maximum number of pixels, that is, the number of pixels cut by the masking process for removing the above-described image noise, the actual read frequency of the image signal after the masking process and the clock frequency of the standard image signal are not equal to each other but shifted from each other. Therefore, in the embodiment, the prescribed clock frequency is set to a frequency, which is slightly lower than the recommended driving frequency (clock) of the imaging device having the maximum number of pixels, so as to correspond to the number of pixels cut by the masking process, so that the prescribed clock frequency may be equal to the read frequency of the image signal after the masking process. For this reason, in the embodiment, the prescribed clock frequency is not set so as to correspond to only the maximum number of pixels read from the imaging device, but the prescribed clock frequency may be appropriately set so as to correspond to the number of pixels approximate to the maximum number of pixels according to content of each process.

Accordingly, the amount of data of the standard image signal is not set so as to be equal to the maximum number of pixels read from the imaging devices 23A and 23B, but the amount of data of the standard image signal may be appropriately set so as to correspond to the number of pixels approximate to the maximum number of pixels according to content of each process such as the number of read pixels which is apparently large to remove noise or the cut amount of the masking process of removing image noise.

In addition, in the embodiment, although the example where the pixel density conversion unit 377 in the signal processing unit 37 performs the process of up-converting the pixel densities of all the image signals so as to be constant amount of data is described, the electronic zoom processing unit 375 may perform the up-converting process of the pixel density conversion unit 377. This is because the electronic zoom processing unit 375 essentially performs an enlargement/reduction process by performing the pixel density conversion and, thus, the electronic zoom processing unit 375 has a function of the pixel density conversion process.

In addition, in the embodiment, although the case where the pixel arrangement of the imaging device is a square pixel type (aspect ratio is 1:1) is described as an example, the embodiment may be applied to any type other than the square pixel type. As a low-density pixel type imaging device having 0.44 mega pixels or the like, a TV signal format type other than the square pixel type, in other words, having an aspect ratio different from 1:1 has been used in the related art. In the case of the TV signal format type imaging sensor, a pixel density conversion for forming square pixels is needed before performing the pixel density conversion process. In addition, in the case where one-side imaging device is of a square pixel type, a process of forming square pixels is needed in order to perform the standard image signal generation process which is common to the signal processing unit 37. For example, in the case of a TV format type having 0.44 mega pixels, a compression process for increasing the number of pixels so as for 752 pixels in the horizontal direction to be 768 pixels needs to be performed. In FIG. 6, although the multiple number in the pixel density conversion process is expressed by a single number, magnification ratios may be set independently of the horizontal and vertical directions, and the pixel density conversion process including the process of forming square pixels can be performed by the pixel density conversion unit 377. Therefore, the embodiment can be applied to even the case where a scope having a TV signal format type imaging device and a scope having a square pixel type imaging device can be selected.

In addition, in FIGS. 4 and 5, although the case where the cut-out process of the effective image data from the standard image signal is performed based on the information on the cut-out area Sa is described, the embodiment is not limited thereto. For example, the information of the position corresponding to the boundary portion of the G-Ac area and the G-Ab area in the lower portion of FIG. 4 is set in the pixel density conversion table, and two clocks of H-G-Ac clock and V-G-Ac clock indicating the boundary (not illustrated) of the cut-out of pixels are transmitted from the signal processing unit 37 to the image generation unit 33 based on the above-described information. The image generation unit 33 may cut out a necessary area corresponding to the effective image data by using the H-G-Ac clock and the V-G-Ac clock indicating the boundary of the cut-out of pixels.

In addition, in FIG. 1, although the case where the two types of the scopes 2A and 2B are connected to the main apparatus 3 is described as an example, the types of the scope is not limited to the two types, but three types or more of the scopes may be connected to the main apparatus 3. In this case, the amount of data of the normalized signal may be set so as to correspond to the image signal generated by the imaging device having the maximum number of pixels among the connectable scopes, and the conversion magnification ratio and the dummy signal supplementing area in the pixel density conversion process and the dummy signal excluding area and the cut-out area of the effective image data in the image generation process may be set according to the number of pixels of the imaging device of each scope.

In addition, although the embodiment can be applied to any one of medical and industrial endoscope systems, since the configuration can be simplified, compact portable endoscope systems can be implemented. In addition, since the endoscope system is powered with a battery, the endoscope system can be very appropriately used as an industrial endoscope system which particularly requires saving power.

According to an embodiment of the present invention, since a standard image signal of a predetermined amount of data, generated by converting a pixel density of an image signal to a high density, is output, merely associating an image signal processing circuit with only the standard image signal is sufficient, and therefore, an apparatus configuration is simplified, and development is easy while resolution of an output image is maintainable.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus for an endoscope, wherein any one of a plurality of insertion units is detachably connectable to the image processing apparatus, the plurality of insertion units respectively having imaging devices with numbers of pixels different from one another installed therein, the image processing apparatus comprising:
   an image signal processing unit that processes an image signal captured by a connected imaging device; and
   an image data generation unit that generates image data, wherein the image signal processing unit:
      converts a pixel density of the image signal to a high density without changing a number of pixels;
      disposes the image signal after conversion to the high density on an image data area in a normalized signal, and disposes a dummy signal on a dummy signal supplementing area in the normalized signal, so as to generate a standard image signal, wherein an amount of data of the standard image signal coincides with an amount of data of the normalized signal; and
      outputs, to the image data generation unit, the standard image signal and a clock signal indicating a boundary of cut-out of the image signal after conversion to the high density, and
   wherein the image data generation unit:
      extracts the image signal after conversion to the high density from the standard image signal, based on the clock signal; and
      generates the image data from the extracted image signal.

2. An image processing method for an endoscope, the image processing method comprising:
   processing an image signal captured by an imaging device of an insertion unit connected to a main apparatus of an endoscope apparatus, wherein the insertion unit is from among a plurality of insertion units any one of which is detachably connectable to the main apparatus, the plurality of insertion units respectively having imaging devices with numbers of pixels different from one another installed therein; and
   generating image data;
   wherein the processing of the image signal includes:
      converting a pixel density of the image signal to a high density without changing a number of pixels;
      disposing the image signal after conversion to the high density on an image data area in a normalized signal, and disposing a dummy signal on a dummy signal supplementing area in the normalized signal, so as to generate a standard image signal, wherein an amount of data of the standard image signal coincides with an amount of data of the normalized signal; and
      outputting the standard image signal and a clock signal indicating a boundary of cut-out of the image signal after conversion to the high density, and
   wherein the generating of the image data includes:
      extracting the image signal after conversion to the high density from the standard image signal, based on the clock signal; and
      generating the image data from the extracted image signal.

3. The image processing apparatus according to claim 1, wherein the image signal processing unit converts the pixel density of the image signal to the high density such that a time for processing data of one pixel of the image signal becomes equal to a time in which the image data generation unit processes data of one pixel of the normalized signal.

4. The image processing apparatus according to claim 1, wherein the image data generation unit generates the image data based on a common constant clock frequency, and
   wherein the image signal processing unit converts the pixel density of the image signal to the high density without changing the number of pixels so as to allow generation of the image data based on the common constant clock frequency.

* * * * *